(12) United States Patent
Alanbaei

(10) Patent No.: US 10,531,867 B2
(45) Date of Patent: Jan. 14, 2020

(54) SINUS VENOSUS ATRIAL SEPTAL DEFECT TREATMENT DEVICE

(71) Applicant: Muath Alanbaei, Safat (KW)

(72) Inventor: Muath Alanbaei, Safat (KW)

( * ) Notice: Subject to any disclaimer, the term of this patent is extended or adjusted under 35 U.S.C. 154(b) by 0 days.

(21) Appl. No.: 15/891,653

(22) Filed: Feb. 8, 2018

(65) Prior Publication Data

US 2018/0228479 A1 Aug. 16, 2018

Related U.S. Application Data

(60) Provisional application No. 62/458,527, filed on Feb. 13, 2017.

(51) Int. Cl.
| | | |
|---|---|---|
| *A61B 17/00* | (2006.01) | |
| *A61F 2/958* | (2013.01) | |
| *A61F 2/82* | (2013.01) | |
| *A61B 90/00* | (2016.01) | |
| *A61B 17/11* | (2006.01) | |

(52) U.S. Cl.
CPC ............ *A61B 17/0057* (2013.01); *A61F 2/82* (2013.01); *A61F 2/958* (2013.01); *A61B 2017/00243* (2013.01); *A61B 2017/00557* (2013.01); *A61B 2017/00575* (2013.01); *A61B 2017/00592* (2013.01); *A61B 2017/00597* (2013.01); *A61B 2017/00606* (2013.01); *A61B 2017/00623* (2013.01); *A61B 2017/00853* (2013.01); *A61B 2017/1107* (2013.01); *A61B 2090/3966* (2016.02); *A61F 2002/825* (2013.01); *A61F 2002/9583* (2013.01); *A61F 2250/0039* (2013.01)

(58) Field of Classification Search
CPC ...... A61F 2/90; A61F 2/958; A61F 2002/821; A61F 2002/828; A61F 2002/9505; A61F 2002/9583; A61F 2/06; A61F 2/07; A61B 2017/00592; A61B 2017/00606; A61B 2017/00623; A61B 17/0057
See application file for complete search history.

(56) References Cited

U.S. PATENT DOCUMENTS

| 8,147,513 | B2 | 4/2012 | Seibold et al. | |
|---|---|---|---|---|
| 9,604,036 | B2 * | 3/2017 | Burton | .................. A61M 25/10 |
| 2007/0055358 | A1 * | 3/2007 | Krolik | ..................... A61F 2/958 |
| | | | | 623/1.31 |

(Continued)

FOREIGN PATENT DOCUMENTS

| AU | 2013270508 A | 1/2014 |
|---|---|---|
| EP | 2 108 315 A2 | 10/2009 |

(Continued)

*Primary Examiner* — Sarah W Aleman
(74) *Attorney, Agent, or Firm* — Winthrop & Weinstine, P.A.; Nadeem W. Schwen

(57) ABSTRACT

The sinus venosus atrial septal defect ("ASD") treatment device includes has a generally tubular or funnel shaped configuration. A first end of the device can have a diameter that is less than a diameter of a second end of the device. The device can be inserted in the right upper right pulmonary vein PV. The second end of the device is configured to expand in a skirt-like configuration once the device is positioned in the right upper right pulmonary vein PV. In this manner, the device closes the upper sinus venosus hole and diverts anomalous pulmonary venous drainage into the left atrium.

18 Claims, 10 Drawing Sheets

(56) References Cited

U.S. PATENT DOCUMENTS

| | | | |
|---|---|---|---|
| 2007/0244494 A1 | 10/2007 | Downing | |
| 2007/0270741 A1 | 11/2007 | Hasset et al. | |
| 2008/0077224 A1* | 3/2008 | Valencia | A61F 2/958 623/1.11 |
| 2011/0022151 A1 | 1/2011 | Shin et al. | |
| 2013/0261734 A1 | 10/2013 | Young et al. | |
| 2013/0317541 A1 | 11/2013 | Singhal et al. | |
| 2014/0277119 A1 | 9/2014 | Akpinar | |
| 2014/0343602 A1 | 11/2014 | Cox et al. | |
| 2015/0039004 A1* | 2/2015 | Sarge | A61B 17/22012 606/169 |
| 2015/0119931 A1 | 4/2015 | Amplatz et al. | |

FOREIGN PATENT DOCUMENTS

| | | |
|---|---|---|
| GB | 2 378 137 A | 2/2003 |
| KR | 10-2009-0122721 A | 12/2009 |
| SU | 407555 | 12/1973 |

\* cited by examiner

SINUS VENOSUS ATRIAL SEPTAL DEFECT TREATMENT DEVICE

CROSS-REFERENCE TO RELATED APPLICATION

This application claims the benefit of U.S. Provisional Patent Application Ser. No. 62/458,527 filed Feb. 13, 2017, which is herein incorporated by reference in its entirety.

BACKGROUND

1. Field

The present disclosure relates to a percutaneous interventional device, and particularly to a sinus venosus atrial septal defect treatment device and method.

2. Description of the Related Art

Typically, in a normal functioning heart, the left atrium receives the oxygenated blood from each of the four pulmonary veins. After receiving it, the oxygenated blood flows into the left ventricle, where the oxygenated blood is subsequently pumped to the brain, organs, and tissues of the body. The right atrium, on the other hand, receives the deoxygenated blood from the superior vena cava and inferior vena cava and other cardiac veins and then pumps deoxygenated blood into the right ventricle, which subsequently pumps the deoxygenated blood into the pulmonary system to replenish its oxygen supply. Normally, the left atrium and the right atrium are separated by a septum known as the interatrial septum that prevents the oxygenated blood in the left atrium from mixing with the deoxygenated blood in the right atrium.

However, if the interatrial septum fails to properly develop an atrial septal defect (ASD) can result. An ASD is a hole in the interatrial septum that allows the oxygenated blood to mix with the deoxygenated blood. If the ASD is left untreated, it can lead to lower than normal oxygen in the atrial blood that is pumped from the left atrium to the brain, organs, and tissues of the body, which can eventually lead to the development of a cardiac arrhythmia, decompression sickness, Eisenmenger's syndrome, paradoxical embolus, and even migraines.

There are four types of ASDs, an ostium secundum ASD, an ostium primum ASD, a sinus venosus ASD, and a coronary sinus ASD, the ostium secundum ASD being the most prevalent. While ostium secundum and ostium primum ASDs account for approximately 70% and 20%, respectively, of the total number of ASDs, sinus venosus ASDs account for approximately 10% of the total number of ASDs. The most common type of sinus venosus ASD occurs at the junction of right atrium and the superior vena cava, which is the location where the pulmonary veins enter the heart. In other words, one of the four pulmonary veins, such as the right upper pulmonary vein, drains into the right atrium instead of the left atrium. While ostium secundum ASD can be treated percutaneously, as well as surgically, to date, there is no percutaneous interventional procedure for treating sinus venosus ASDs.

Thus an atrial septal defect treatment device and method solving the aforementioned problems is desired.

SUMMARY OF THE INVENTION

The sinus venosus atrial septal defect ("ASD") treatment device includes a flexible proximal portion at a first end, a flexible distal portion at an opposing second end, and a flexible central portion between the proximal portion and the distal portion. The device has a hollow lumen and is open at opposing ends thereof. The opening at the first end is expandable from a first diameter when the device is being deployed through the body of the left atrium, to a second, larger diameter when the device is positioned within the right upper pulmonary vein and expanded with a balloon catheter. The proximal portion includes a plurality of receiving plates with respective keyholes configured to receive a corresponding key from a balloon portion of a balloon catheter. The distal portion includes a self-expandable edge portion or skirt. The skirt can include a septal augmenter rim configured for securing the device to the left atrium side of the interatrial septum.

These and other features of the disclosed technology will become readily apparent upon further review of the following specification and drawings.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 6:
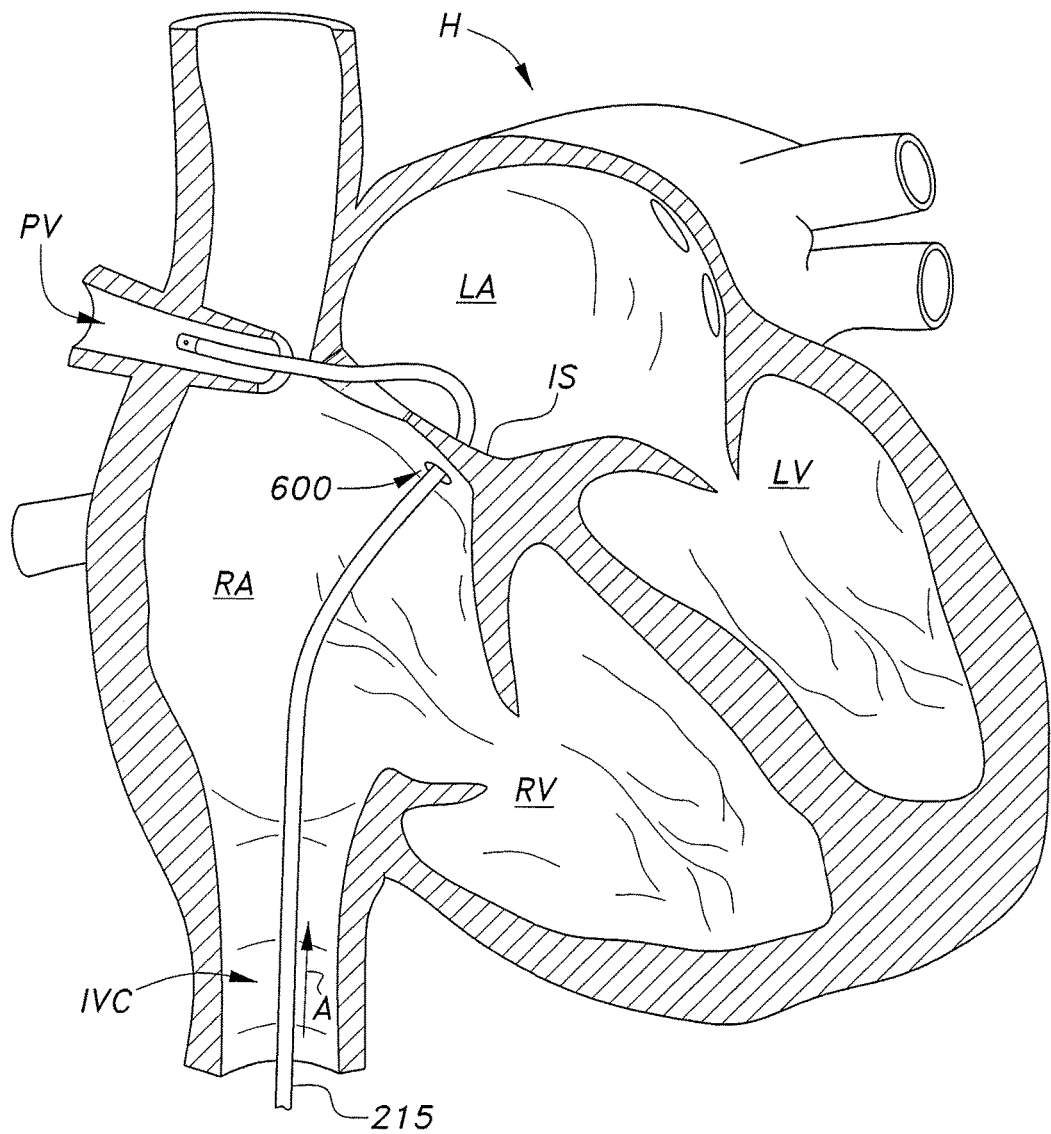
FIG. 6 illustrates the second sheath utilized to position the atrial septal defect device in the pulmonary vein of the heart having a sinus venosus ASD.
Figure 7A:
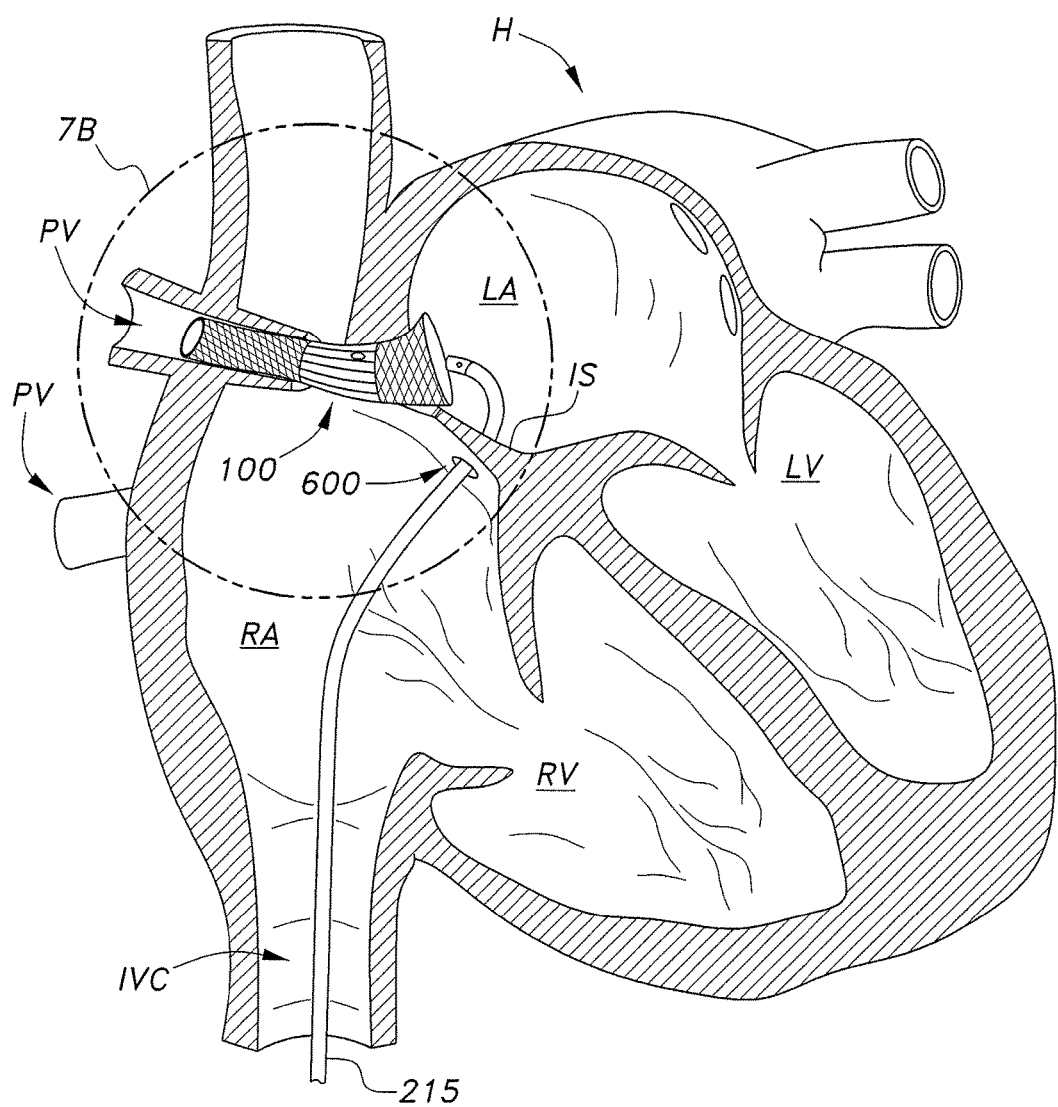
FIG. 7A illustrates the atrial septal defect treatment device extending from the pulmonary vein into the left atrium via the interatrial septum of the heart having a sinus venosus ASD.
Figure 7B:
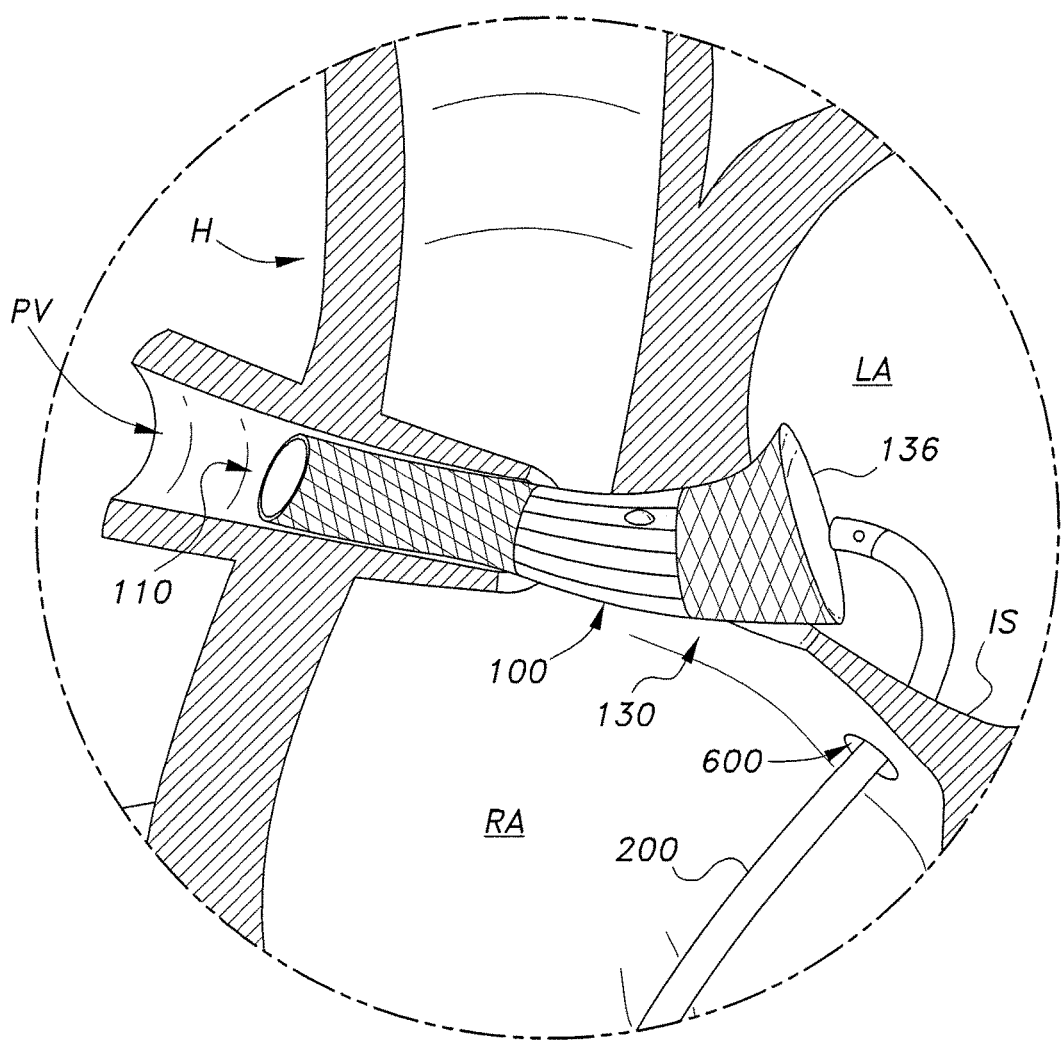
FIG. 7B is an exploded view of the view illustrated in FIG. 7A.

Referring to FIGS. 1A-7B, an atrial septal defect treatment device 100, configured for the percutaneous closure of a sinus venosus atrial septal defect for diversion of anomalous pulmonary drainage into the left atrium, is generally illustrated. The device 100 has a generally tubular or funnel shaped configuration. A first end 122 of the device 100 can have a diameter that is less than a diameter of a second end 124 of the device 100. The device 100 can be inserted in the right upper right pulmonary vein PV. The second end 124 of the device 100 is configured to expand in a skirt-like configuration once the device 100 is positioned in the right upper right pulmonary vein PV. In this manner, the device 100 closes the upper sinus venosus hole and diverts anomalous pulmonary venous drainage into the left atrium, as illustrated in FIGS. 7A and 7B.

The device 100 includes a flexible proximal portion 110 at the first end 122, a flexible distal portion 130 at the opposing second end 124, and a flexible central portion 120 between the proximal portion 110 and the distal portion 130. The device 100 has a hollow lumen and is open at opposing ends 122, 124 thereof.

The proximal portion 110 can have any suitable shape, such as a generally cylindrical shape. The proximal portion 110 includes a self-expanding mesh 112 that can be formed from any suitable interlocking medical grade material, such as Nitinol. An opening 119 at the first end 122 is expandable from a first diameter D1 (FIG. 1A), such as when the device 100 is being deployed through the body of the left atrium, to a second, larger diameter D1' (FIGS. 1B and 1C), such as when the device 100 is positioned within the right upper pulmonary vein and expanded using a balloon catheter. The second diameter can range, for example, from about 10 mm to about 15 mm. The proximal portion 110 can have any suitable length L1, such as a length ranging from about 15 mm to about 20 mm. In an embodiment, the proximal portion 110 can include a plurality of attachment receiving structures or receiving plates 114 for receiving a corresponding attachment device or key. For example, each of the receiving plates 114 can include an aperture or keyhole 116. The keyhole 116 can include a circular first portion 117*a* and rectangular second portion 117*b* extending from the first portion 117*a*. The keyhole 116 is configured to receive a corresponding key from a balloon portion of a balloon catheter, as will be further described in detail below. The plurality of plates 114 can include three plates 114, such as metal plates, vertically positioned around the proximal portion 110 of the device 100.

The central portion 120 of the device 100 can have any suitable length L2, such as a length ranging from approximately 10 mm to approximately 15 mm. The central portion 120 can include a plurality of flexible, e.g., self-expandable, metal rods 126. The metal rods can be spaced from each other. Each metal rod 126 can be formed from any suitable medical grade material, such as Nitinol, and may be covered by any type of suitable medical grade material, such as polytetrafluoroethylene. The central portion 120 also includes an aperture 128 that remains uncovered for side branch stenting in case of the need for extra support or for bifurcating drainage. The edge or area immediately surrounding the aperture 128 may be radio-opaque. The aperture 128 can have any suitable diameter, such as a diameter of approximately 5 mm.

The distal portion 130 can have any suitable length L3, such as 10 mm. The distal portion 130 includes a self-expandable edge portion or skirt 132 formed from a plurality of interlocking metal rods 134, such as Nitinol rods, that can be arranged in a grid formation or in a mesh formation. Each of the metal rods 134 may be covered, such as partially covered, with polytetrafluoroethylene. For example, an end of each metal rod 134 attached to the central portion 120 may be covered with polytetrafluoroethylene and an opposing end of each metal rod 134 may be left bare (i.e. uncovered).

The skirt 132 of the opposing distal portion 130 can have any suitable diameter, such as a first diameter D3 when collapsed and positioned on the balloon 202 of the balloon catheter 200 and a second larger diameter D3' (FIG. 1C) when expanded to occlude the sinus venosus atrial septal defect (e.g. opening) from the left atrium LA side of the interatrial septum IS. When the sinus venosus atrial septal defect (e.g. opening) is occluded in this manner, oxygenated blood can flow directly into the left atrium LA of the heart H without escaping into the right atrium RA. The skirt 132 can include an expandable septal augmenter rim 136. The septal augmenter rim 136 is configured for securing the device 100 to the left atrium LA side of the interatrial septum IS once the septal augmenter rim 136 is inserted into the left atrium LA side of the interatrial septum IS. Once expanded, the septal augmenter rim 136 can anchor the opposing distal portion 130 of the device 100 within the left atrium LA side of the interatrial septum IS.

Figure 1A:
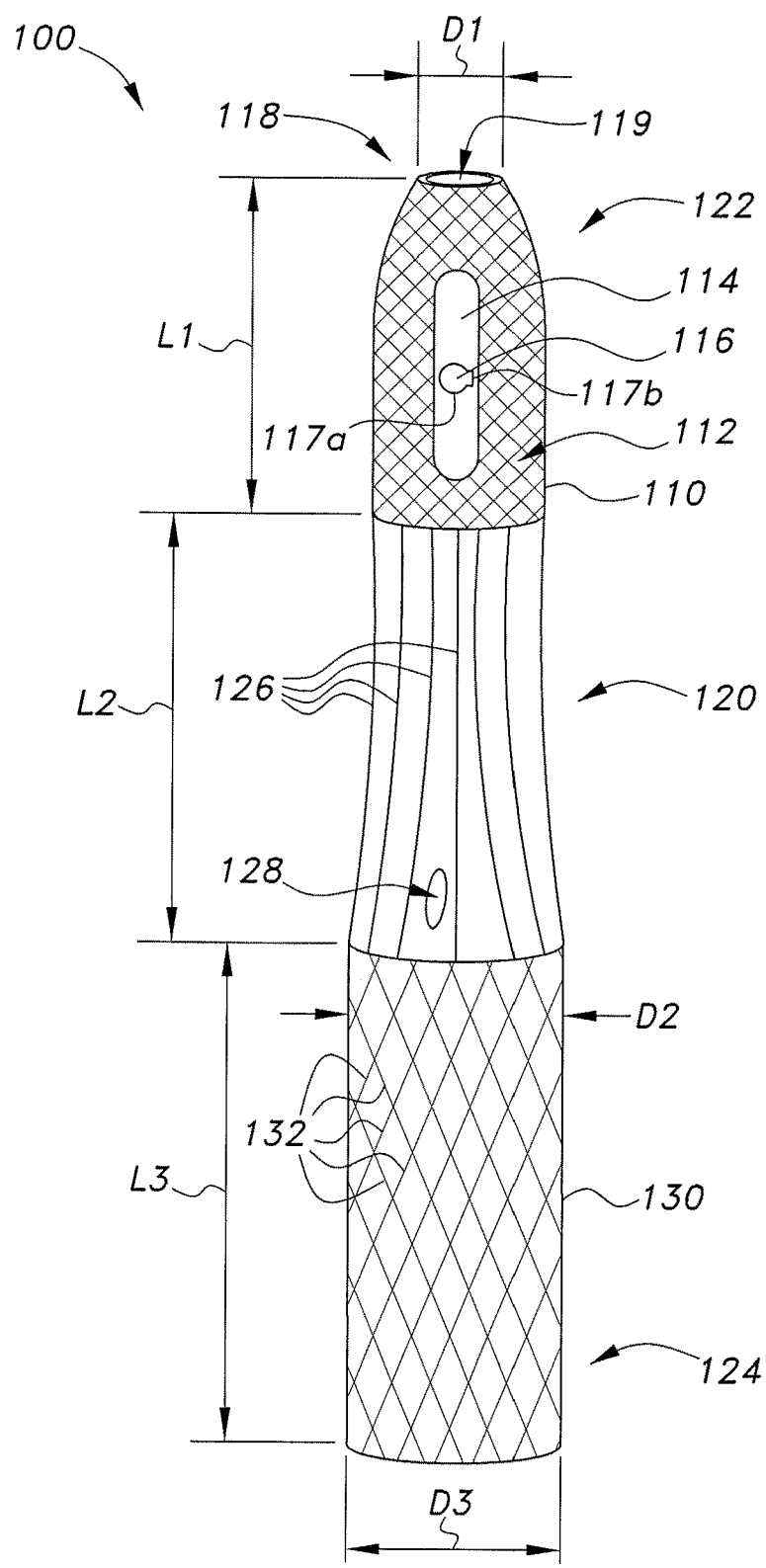
FIG. 1A is an environmental side view of an atrial septal defect treatment device in collapsed form.
Figure 1B:
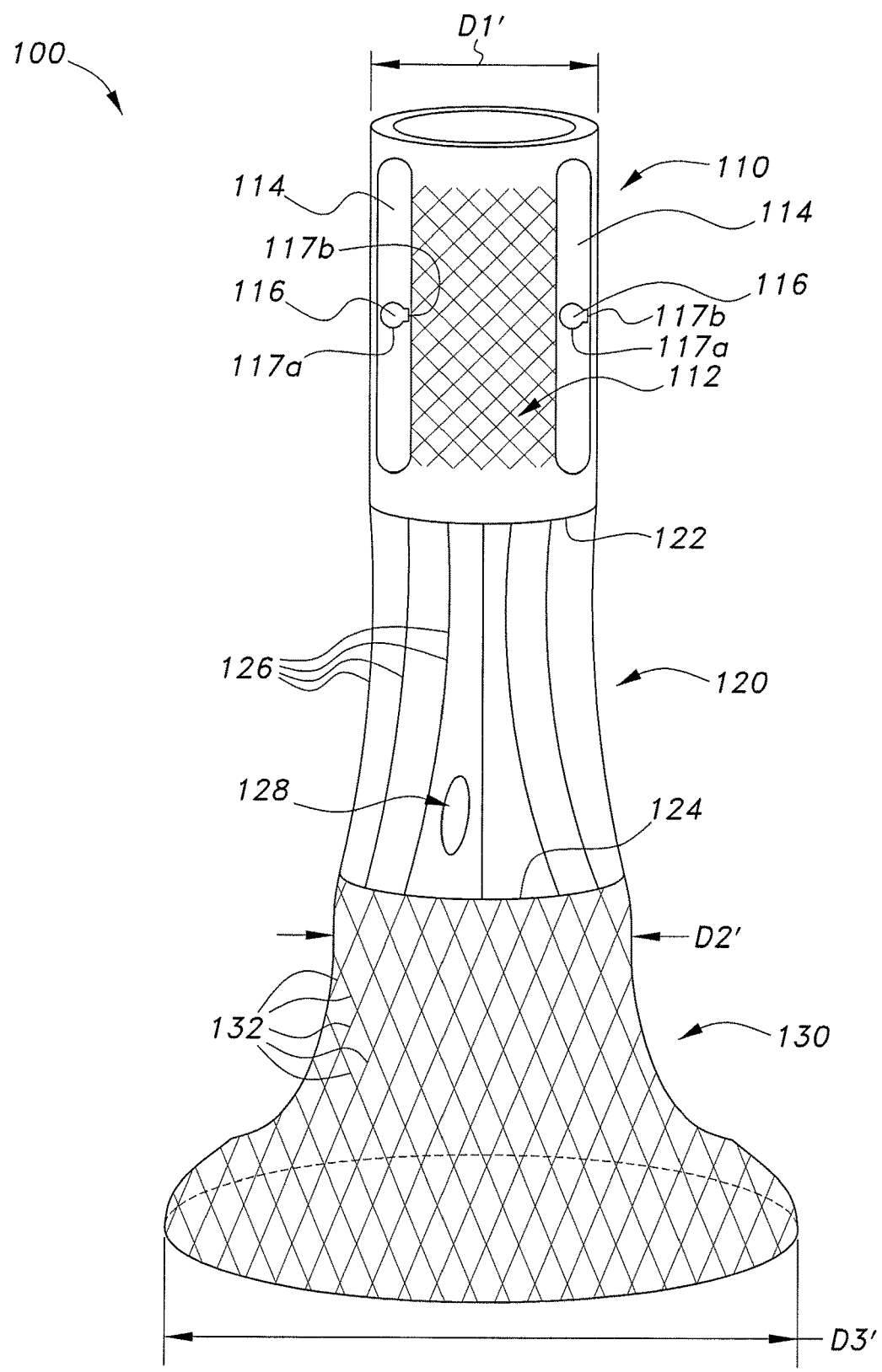
FIG. 1B is another environmental side view of the atrial septal defect treatment device in expanded form.
Figure 1C:
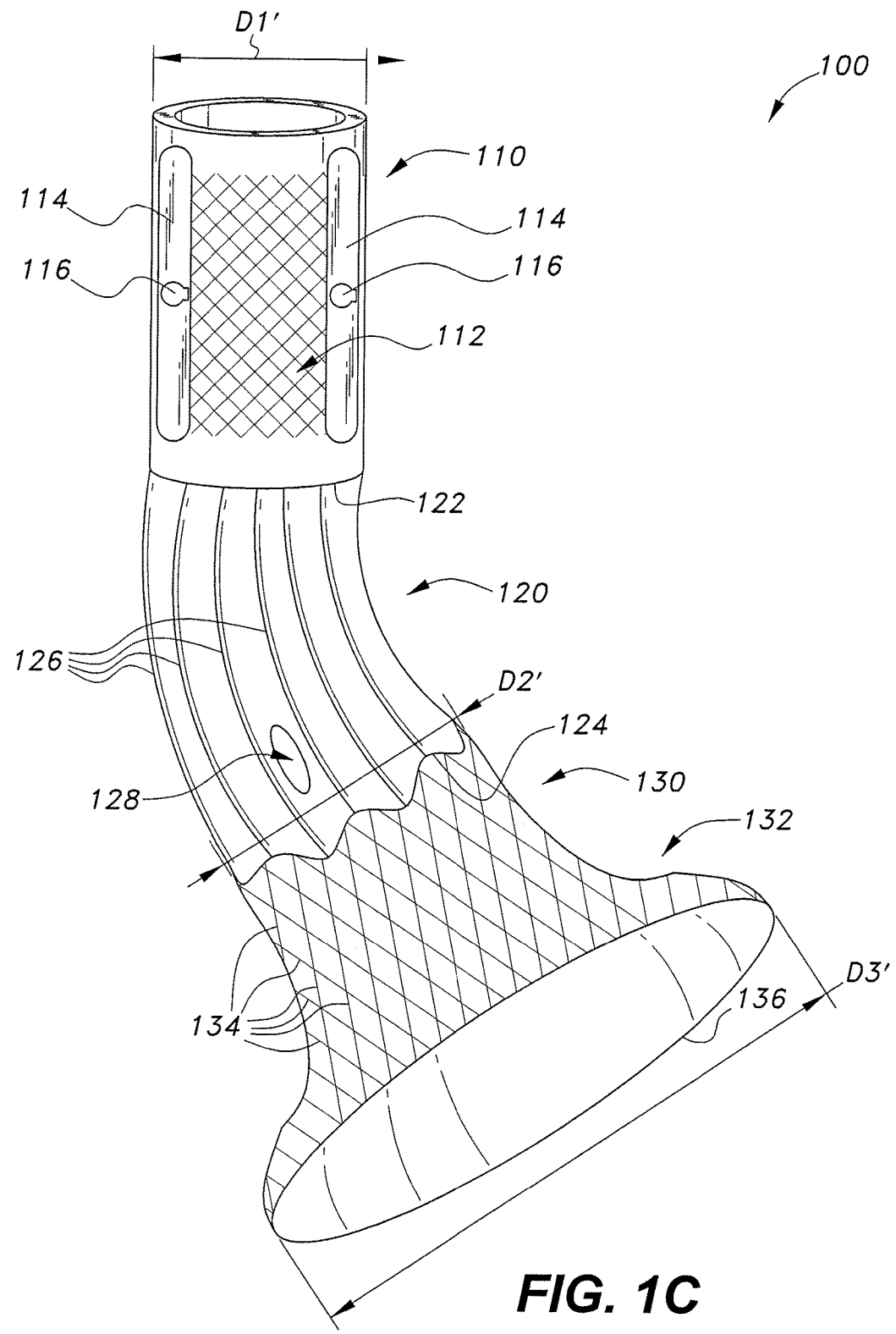
FIG. 1C illustrates the configuration of the atrial septal defect device expanded within a pulmonary vein of a heart.
Figure 2:
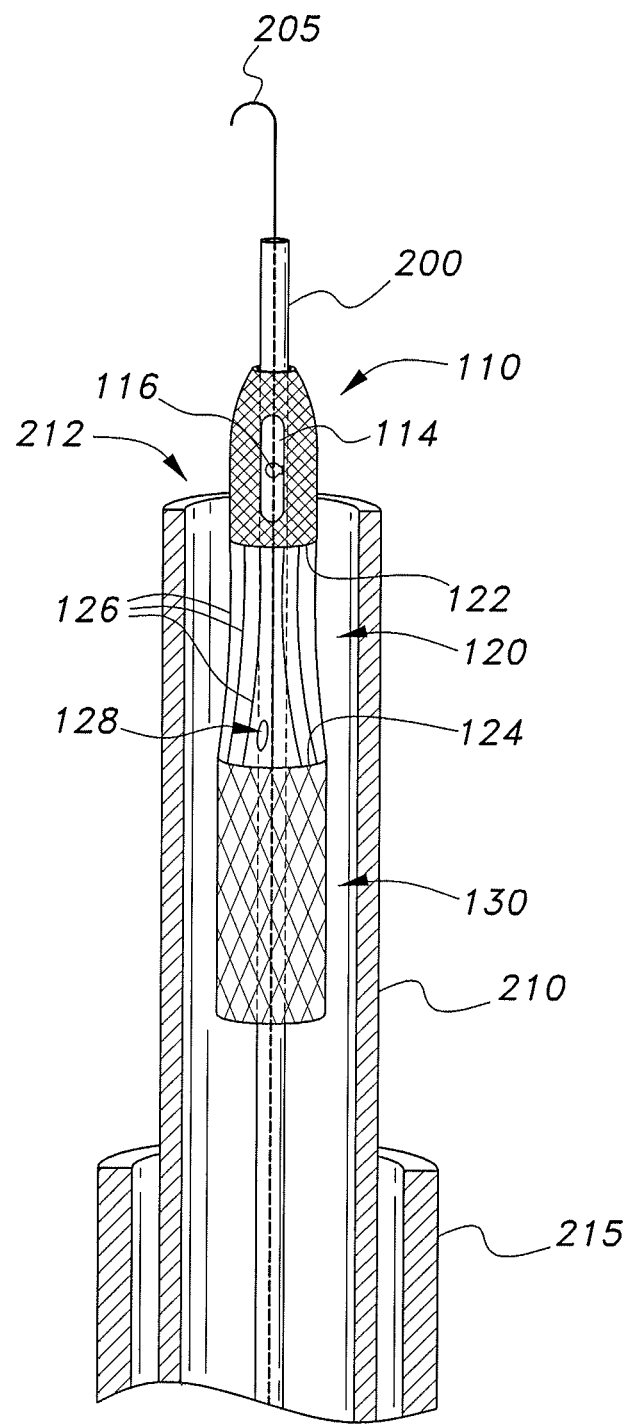
FIG. 2 illustrates the atrial septal defect device positioned on a balloon catheter positioned on a guide wire.
Figure 3:
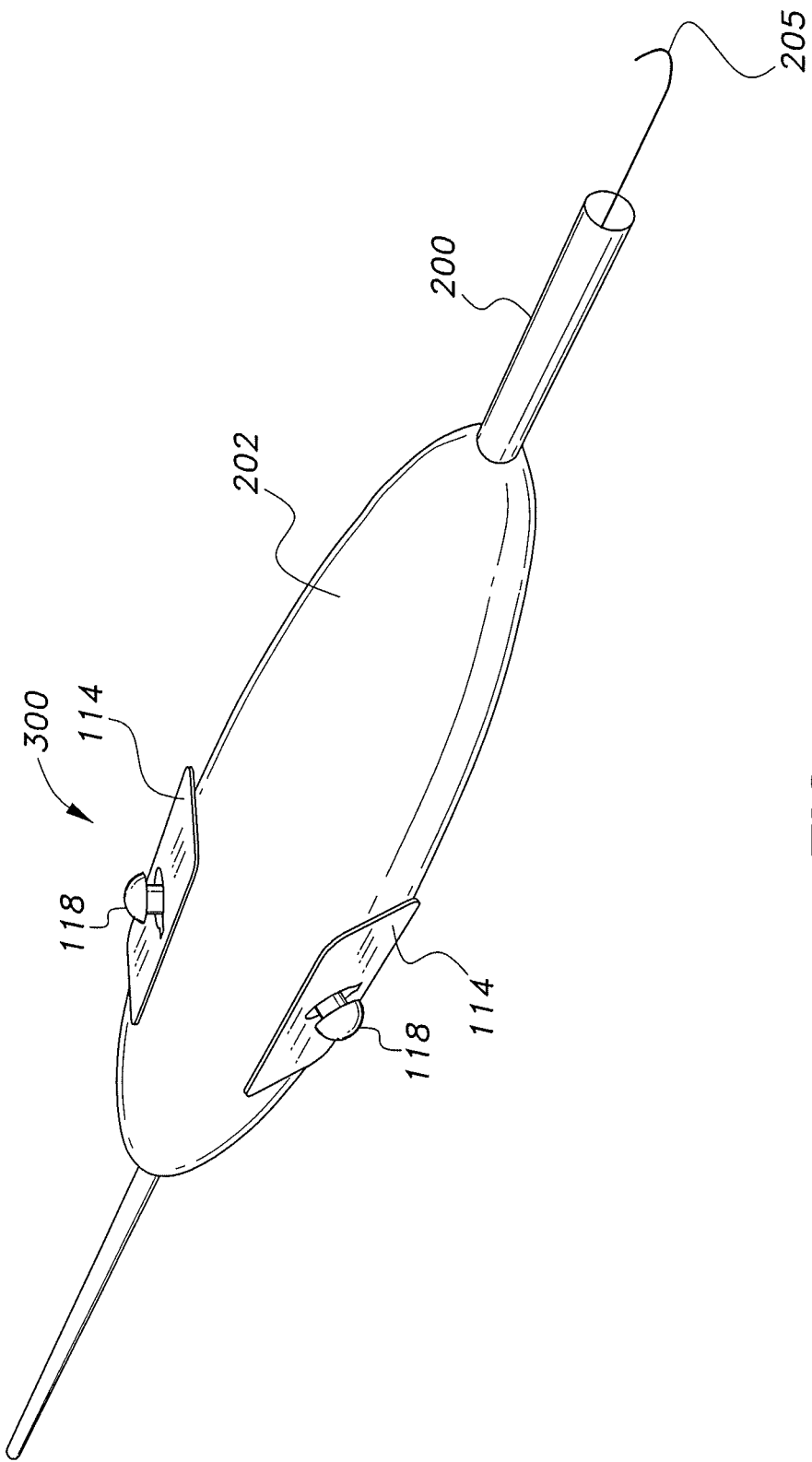
FIG. 3 illustrates a locking system for securing the atrial septal defect treatment device to a balloon of a balloon catheter.
Figure 4:
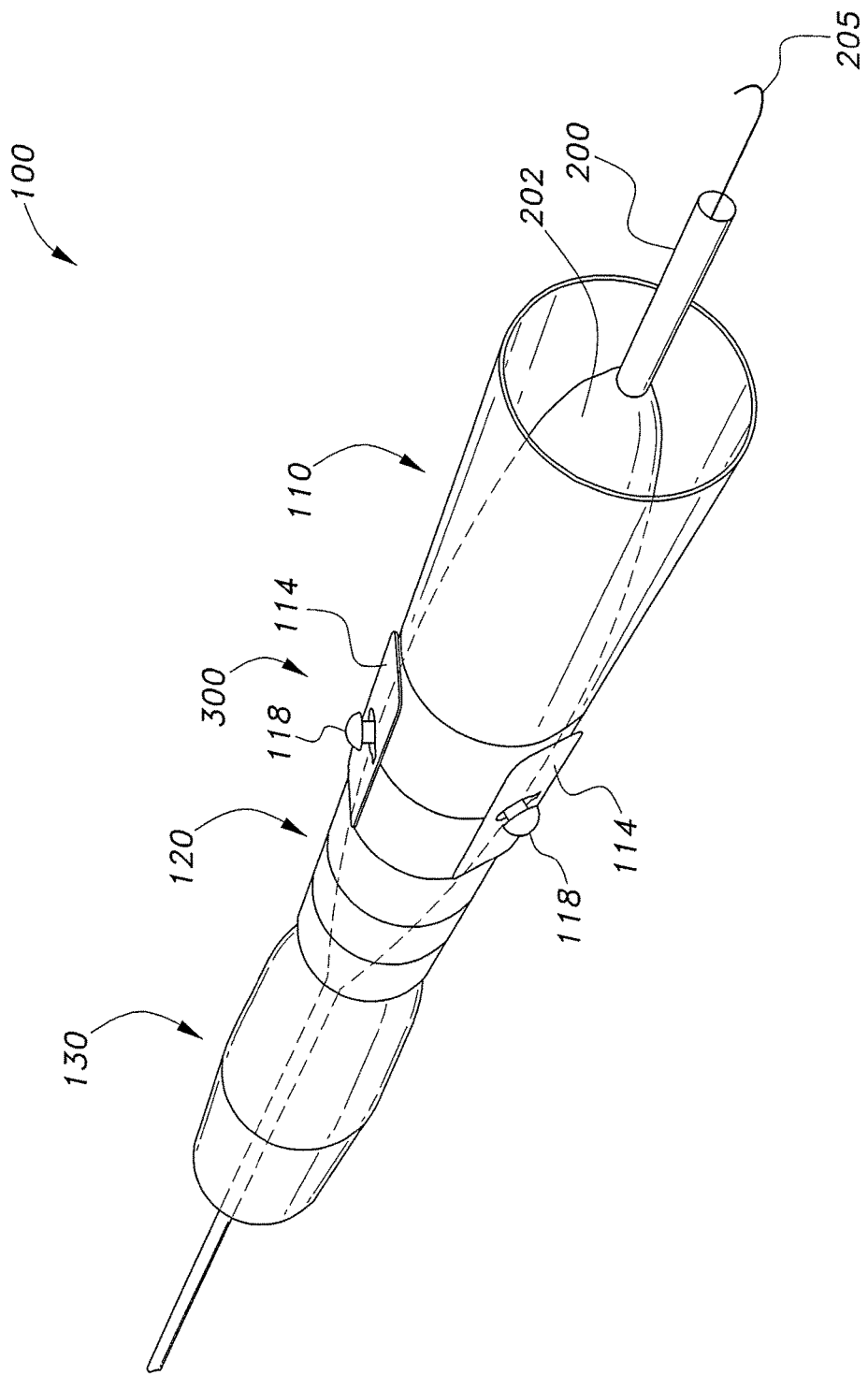
FIG. 4 illustrates the atrial septal defect treatment device secured to the balloon of the balloon catheter via the locking system.
Figure 5:
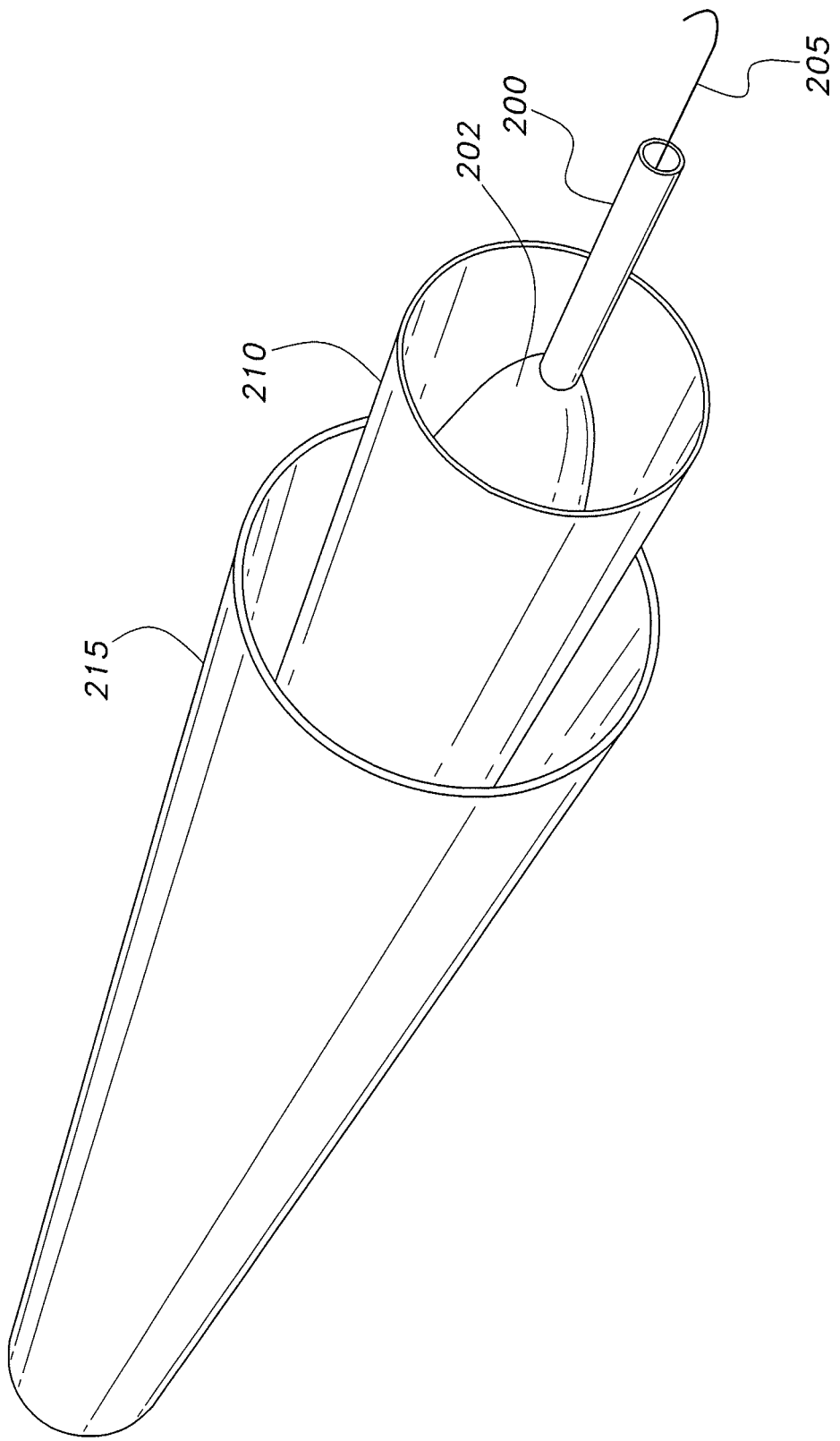
FIG. 5 illustrates the balloon catheter positioned on the guide wire, the balloon catheter and the corresponding guide wire being positioned within a second sheath, the second sheath being positioned with a first sheath used to position the atrial septal defect treatment device within the pulmonary vein.

The device may be positioned in the right upper right pulmonary vein PV using a balloon catheter 202 (FIG. 3 and FIG. 4). A balloon portion 202 of the balloon catheter 200 includes attachment structures or locking plates with one or more keys 118, e.g., radio-opaque mushroom shaped keys (FIG. 4) configured for insertion in respective keyholes 116 of the device 100. Each keyhole 116 is suitable for receiving a corresponding key 118, such as a mushroom shaped key with circular head and stem extending therefrom. The balloon catheter 205 is inserted into the device 100 outside of the body, via the distal portion 130 of the device 100, to secure the device 100 thereto. Each key 118 fits into a corresponding keyhole 116 of each plate 114. Clockwise rotation of the catheter moves the stem of the mushroom key to fit in the keyhole second portion 117*b* so as to secure the device 100 to the balloon 202 of the balloon catheter 200 to facilitate delivering the device 100 within the pulmonary vein PV of the heart H. It should be understood that the key/keyhole attachment described herein is provided as a non-limiting example. The attachment structures can include any structure which allows the catheter to engage the device 100.

By way of operation, initially a trans-femoral vein approach is used by advancing a first sheath 215, e.g., a large caliber deflectable/steerable sheath having a size ranging from 9 Fr to 12 Fr, into the femoral artery and toward the interatrial septum IS (FIG. 6). This is followed by making a trans-septal opening 600 with a trans-septal needle (not shown), just below the sinus venosus atrial septal defect (ASD) in the interatrial septum IS separating the right atrium RA from the left atrium LA (FIG. 7).

The trans-septal opening 600 allows for vascular access, as well as access into the target pulmonary vein PV. In this manner, pulmonary vein PV may be targeted via the inferior vena cava IVC, as illustrated by arrow A in FIG. 6. The steerable sheath 215 is configured for supporting and providing access into the pulmonary vein PV from the left atrium LA, via the interatrial septum IS, as illustrated in FIG. 6. Such steerable sheaths are well known in the art and can include the Agilis™ NXT Steerable Introducer from St. Jude, the FlexCath Advance Steerable Sheath from Medtronic, and the Vado® Steerable Sheath from Abbott.

A guide wire 205, e.g., an elongated stiff "J" tip guide wire, is then advanced through the steerable sheath 215 to the coronary arteries. The steerable sheath 215 is used to properly position the guide wire 205 within the target pulmonary vein PV. Once the guide wire 205 is properly positioned, a second sheath 210 including a tip 212 with a radio-opaque marker is inserted within the steerable sheath 215, over the guide wire 205, and into the target pulmonary vein PV via the left atrium LA.

Once the second sheath 210 is properly positioned within the target pulmonary vein PV, the balloon catheter 200, secured to the device 100 via locking system 300, is then inserted through the second sheath 210 and over the guide wire 205 until the balloon catheter 200 reaches the target pulmonary vein PV. The balloon 202 is then inflated, such as by filling the balloon 202 with fluid, such as saline, as is known in the art. By inflating the balloon 202, the proximal portion 110 of the device 100 expands within the target pulmonary vein PV so as to fit securely within the target pulmonary vein PV. Once the balloon is inflated, the catheter 200 is disengaged (e.g. unlocked) from the device 100, such as by twisting the catheter 200 to remove the keys 118 from the keyholes 116.

After the balloon 202 is disengaged from the proximal portion 110 of the device 100, the second sheath 210 and the balloon catheter 200 are retracted along the guide wire 205 back through the atrial septal defect. As the balloon catheter 200 and the second sheath 210 are retracted, the self-expandable skirt 132 of distal portion 130 of the device 100 expands on the left atrium LA side of the interatrial septum IS, as illustrated in FIGS. 7A and 7B. After expanding within the left atrium LA side of the interatrial septum IS, the septal augmenter rim 136 may anchor the distal portion 136 within the left atrium LA side of the interatrial septum IS to prevent oxygenated blood from flowing into the right atrium RA. Once the proximal portion 110 of the device 100 is properly positioned within the target pulmonary vein PV and the opposing distal portion 130 of the device 100 is properly positioned on the left atrium LA side of the interatrial septum IS, the oxygenated blood may flow from the lungs, through the target pulmonary vein PV and into the left atrium LA of the heart H.

It is to be understood that the disclosed technology is not limited to the embodiments described above, but encompasses any and all embodiments within the scope of the following claims.

I claim:

1. A sinus venosus atrial septal defect treatment device for use with a balloon catheter, comprising:
    a tubular body having a longitudinal axis and opposed first and second open ends, the body defined by:
    a proximal portion having an expandable peripheral wall, the expandable peripheral wall of the proximal portion including a plurality of receiving plates spaced about the peripheral wall, each of the receiving plates including a keyhole therethrough, the keyhole being configured to receive a corresponding key from the balloon catheter,
    wherein the corresponding key includes a stem adjacent to a balloon portion of the balloon catheter and a head directly coupled to the stem opposite the balloon portion, wherein the stem provides a smaller cross section than the head,
    wherein the keyhole includes a first portion configured to receive the head and a portion of the stem therethrough and a narrower second portion configured to receive the portion of the stem,
    wherein the second portion of the keyhole is smaller than the cross section of the head such that the keyhole is configured to be engaged by the key when the stem is positioned in the narrower second portion of the keyhole;
    a distal portion, the distal portion having a distal end and a proximal end, the distal portion having an expandable peripheral wall made from self-expanding mesh, the expandable peripheral wall of the distal portion including an expandable septal augmenter rim at the distal end thereof; and
    a central portion between the proximal portion and the distal portion, the central portion including an expandable peripheral wall.

2. The sinus venosus atrial septal defect treatment device according to claim 1, wherein a diameter of the second open end is larger than a diameter of the first open end.

3. The sinus venosus atrial septal defect treatment device according to claim 1, wherein the peripheral wall of the proximal portion comprises a self-expanding mesh.

4. The sinus venosus atrial septal defect treatment device according to claim 3,
    wherein the self-expanding mesh of the peripheral wall of the proximal portion is formed from metal, and
    wherein the self-expanding mesh of the peripheral wall of the distal portion is formed from metal.

5. The sinus venosus atrial septal defect treatment device according to claim 1, wherein the proximal portion has a length ranging from about 15 mm to about 20 mm.

6. The sinus venosus atrial septal defect treatment device according to claim 1, wherein the central portion has a length ranging from about 10 mm to about 15 mm.

7. The sinus venosus atrial septal defect treatment device according to claim 1, wherein the expandable peripheral wall of the central portion includes an aperture extending through a portion thereof, wherein the aperture is surrounded by a radio-opaque material.

8. The sinus venosus atrial septal defect treatment device according to claim 1, wherein the distal portion has a length of about 10 mm.

9. The sinus venosus atrial septal defect treatment device according to claim 1, wherein each of the plurality of receiving plates is made from metal.

10. The sinus venosus atrial septal defect treatment device according to claim 1, wherein each of the plurality of receiving plates is longitudinally aligned with the longitudinal axis of the tubular body.

11. The sinus venosus atrial septal defect treatment device according to claim 1,
    wherein the peripheral wall of the central portion comprises elongated flexible metal rods about the peripheral wall, each of the elongated flexible metal rods extending from the distal portion to the proximal portion, and
    wherein the central portion is at least as long as the distal portion.

12. The device of claim 1,
    wherein the keyhole is configured for disengagement with the key by twisting of the balloon catheter to locate the stem within the first portion of the keyhole, and
    wherein the keyhole is configured for engagement with the key by twisting of the balloon catheter to locate the stem within the narrower second portion of the keyhole.

13. The sinus venosus atrial septal defect treatment device according to claim 11, wherein the elongated flexible metal rods of the central portion are longitudinally aligned with the longitudinal axis of the tubular body.

14. An assembly comprising:
    a balloon catheter including a balloon portion with protruding keys extending therefrom, each of the keys including a stem adjacent to the balloon portion and a head directly coupled to the stem, wherein for each of the keys, the stem provides a smaller cross section than the head; and
    a tubular body having opposed first and second open ends, the body defined by:

a proximal portion mounted over the balloon portion, the proximal portion having an expandable peripheral wall, the expandable peripheral wall of the proximal portion including a plurality of receiving plates spaced about the peripheral wall, each of the receiving plates including a keyhole therethrough, the keyhole being configured to receive a corresponding key from the balloon catheter, wherein the keyhole includes a first portion configured to receive the head and a portion of the stem therethrough and a narrower second portion configured to receive the portion of the stem, wherein the second portion of the keyhole is smaller than the cross section of the head such that the keyhole is engaged by the key with the stem is positioned in the narrower second portion of the keyhole;

a distal portion, the distal portion having a distal end and a proximal end, the distal portion having an expandable peripheral wall made from self-expanding mesh, the expandable peripheral wall of the distal portion including an expandable septal augmenter rim at the distal end thereof; and a central portion between the proximal portion and the distal portion, the central portion including an expandable peripheral wall.

15. The assembly according to claim 14, wherein the peripheral wall of the proximal portion comprises a self-expanding mesh.

16. The assembly according to claim 14,
wherein the keyhole is configured for disengagement with the key by twisting of the balloon catheter to locate the stem within the first portion of the keyhole, and
wherein the keyhole is configured for engagement with the key by twisting of the balloon catheter to locate the stem within the narrower second portion of the keyhole.

17. The assembly according to claim 14,
wherein the self-expanding mesh of the peripheral wall of the proximal portion is formed from metal, and
wherein the self-expanding mesh of the peripheral wall of the distal portion is formed from metal.

18. The assembly according to claim 14,
wherein the peripheral wall of the central portion comprises elongated flexible metal rods about the peripheral wall, each of the elongated flexible metal rods extending from the distal portion to the proximal portion, and
wherein the central portion is at least as long as the distal portion.

* * * * *